United States Patent
Maître et al.

(10) Patent No.: US 7,303,394 B2
(45) Date of Patent: Dec. 4, 2007

(54) HAND-HELD PIECE FOR DENTAL OR SURGICAL USE INCLUDING A RESILIENT CLAMP

(75) Inventors: Luc Maître, Epauvillers (CH); Cyril Ryser, Tramelan (CH)

(73) Assignee: Bien-Air Holding S.A., Bienne (CH)

( * ) Notice: Subject to any disclaimer, the term of this patent is extended or adjusted under 35 U.S.C. 154(b) by 0 days.

(21) Appl. No.: 11/424,355

(22) Filed: Jun. 15, 2006

(65) Prior Publication Data

US 2006/0286504 A1    Dec. 21, 2006

(30) Foreign Application Priority Data

Jun. 15, 2005    (EP)    ................................. 05012853

(51) Int. Cl.
*A61C 1/14*    (2006.01)
(52) U.S. Cl. ........................................ 433/129; 433/127
(58) Field of Classification Search ................. 433/127, 433/129; 279/43, 51
See application file for complete search history.

(56) References Cited

U.S. PATENT DOCUMENTS 4,874,314 A * 10/1989 Fleer et al. ................. 433/129
5,165,896 A * 11/1992 Hain et al. .................. 433/129

FOREIGN PATENT DOCUMENTS

| DE | 29 05 484 A1 | 8/1979 |
| EP | 0 276 259 A1 | 7/1988 |
| EP | 0 505 599 A1 | 9/1992 |

OTHER PUBLICATIONS

European Search Report issued in corresponding application No. EP 05 01 2853 completed Nov. 11, 2005.

* cited by examiner

*Primary Examiner*—Ehud Gartenberg
*Assistant Examiner*—Heidi M Bashaw
(74) *Attorney, Agent, or Firm*—Griffin & Szipl, P.C.

(57) ABSTRACT

In a hand held piece for dental or surgical use comprising a resilient clamp (20) for holding the cylindrical shank (16) of a tool, the height of the head (3) of the piece can be reduced owing to an inverted arrangement of the clamp in relation to the arrangement of the prior art. The clamp is slideably mounted in a hollow shaft (6), its flexible jaws (31) being directed forwards to enter into contact with a loosening sleeve (19) fixed in a front end of the shaft, i.e. on the tool side. The clamp is longitudinally connected to a pusher (22) manually activated by the operator for opening the clamp. A snap fit device (28) offers a higher initial resistance to movement of the clamp than the standard minimum axial pull force of the tool.

10 Claims, 5 Drawing Sheets

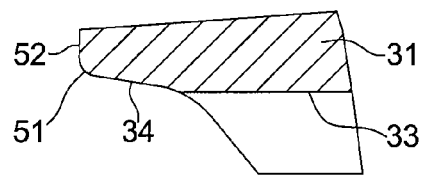
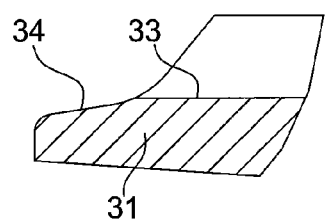
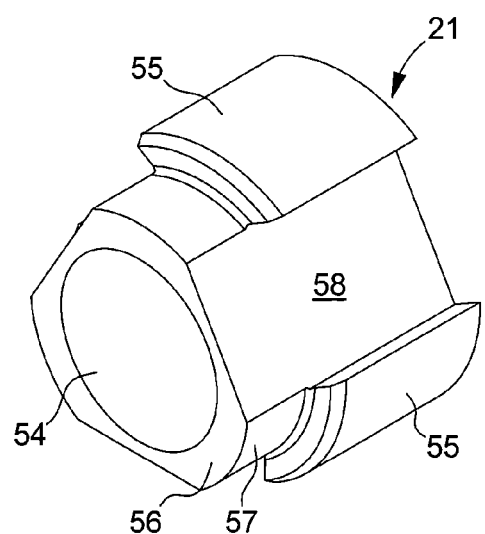
Fig. 5
Fig. 6
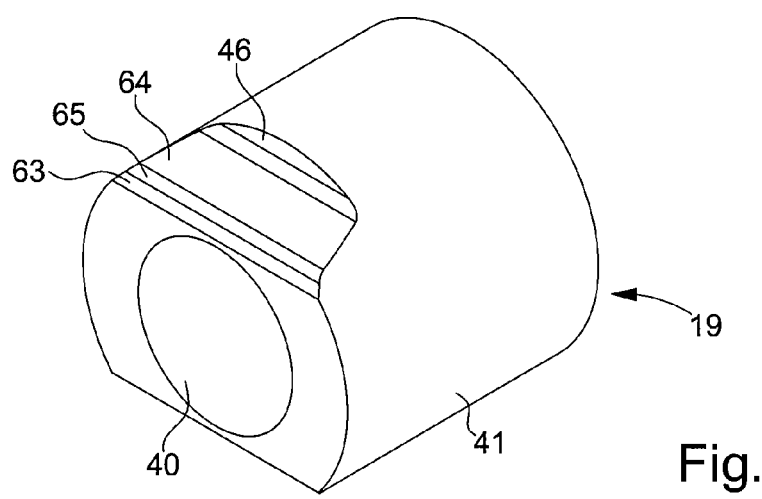
Fig. 7

HAND-HELD PIECE FOR DENTAL OR SURGICAL USE INCLUDING A RESILIENT CLAMP

This application claims priority from European Patent Application No. 05012853.7, filed Jun. 15, 2005, the entire disclosure of which is incorporated herein by reference.

BACKGROUND OF THE INVENTION

The present invention concerns a hand held piece for dental or surgical use, comprising a hollow shaft, associated with rotational drive means and in which there are mounted a clamp for gripping the shank of a removable tool, a loosening sleeve and a sliding pusher placed in a rear end of the hollow shaft and controlled by a manual button to move the clamp and the loosening sleeve closer to each other, the clamp including an annular part and jaws arranged for gripping the shank of the tool by resilience in a working position, the jaws extending longitudinally from the annular part towards the loosening sleeve, which comprises oblique external surfaces able to abut against the free ends of the jaws to move them apart.

In most cases, hand held pieces of this type are driven by an air turbine and rotate at very high speeds, of up to more than 400,000 revolutions per minute, which imposes high requirements on the centring of the tool in relation to the axis of rotation. In order to ensure sufficient holding of the tool while working, the resilient clamp has to resist a standard pull strength of at least 22 N on the tool. Moreover, since the operator has to change tools frequently, this operation must be easy and cause the least possible wear.

In a typical hand held dental piece of this type, as disclosed for example in EP Patent Nos. 273 259 and 505 599, the clamp is fixed in the hollow shaft, its annular part is on the tool side, i.e. at the front end of the shaft, and its jaws extend axially backwards, where the loosening sleeve can slide into the hollow shaft via the effect of a manual pusher connected to the mobile back cover of the hand held piece. The loosening sleeve comprises at the front an external cone provided with support surfaces having a larger angle of aperture than the opposite surfaces of the inner cone of the clamp jaws, such that the contact between the two cones occurs along a line which does not change place on each jaw during the travel of the pusher.

With the design according to EP Patent No. 273 259, the annular part of the clamp centres the tool shank at the front end of the rotating part, whereas the back end of the shank is centred inside the loosening sleeve. Since this part slides, it necessarily has a slight radial play and centring is therefore not excellent. Moreover, manufacturing and balancing the piece that forms both the clamp and the guide bush are difficult and expensive operations. Another drawback of this arrangement lies in the total length of the assembly comprising the clamp, said sleeve and the manual pusher. The length means that the head of the hand held piece must have a certain height, which is inconvenient since this is the part that the dentist has to put in the patient's mouth.

EP Patent No. 505 599 proposes improving this design by means of a guide bush at the front and a fixed guide arranged at the back end of the hollow shaft, thus centring the tool shank better and comprising, inside, a fixed stop member for the tool shank, but the length of the assembly is thereby increased. Further, this arrangement has another drawback, in that the loosening sleeve can become blocked by friction in the open clamp, and it is unable to be unblocked by inserting the tool shank, since the axial stop member is not on the sleeve.

SUMMARY OF THE INVENTION

The present invention concerns a novel arrangement of the elements contained in the hollow shaft, particularly the clamp and its control members, ensuring both a high level of centring precision, reliable working and above all, a construction of shorter length, thus enabling the head of the hand held piece to be made in a particularly compact shape.

There is therefore provided a hand held piece of the type specified in the preamble hereinbefore, characterized in that the loosening sleeve is mounted in a front end of the hollow shaft, i.e. on the tool side, and in that the clamp is slideably mounted in the shaft, its jaws being directed forwards, the clamp being longitudinally connected to the pusher, which enables an operator to move the clamp forwards in order to press against the loosening sleeve. The latter can thus be fixed in the hollow shaft and form a front guide bush for the tool shank. According to one embodiment that ensure excellent guiding of the back end of the shank, a back guide bush provided with a cylindrical bore is fixedly mounted in the hollow shaft, between the annular part of the clamp and the transverse wall of the control pusher, and the bushing includes channels for longitudinal arms connecting the pusher to the clamp.

Owing to these arrangements, it is possible to reduce the length of the rotating assembly relative to the prior art, and thus to obtain a hand held piece whose head has the lowest possible height, without compromising the centring precision of the tool. The elements contributing to this are, in particular, the fact that the dual function of the fixed loosening sleeve also acting as guide bush makes a saving of one piece along the length of the shaft, and the fact that the end of the tool shank can go almost as far the back end of the shaft.

Since the clamp is mobile in an axial direction, any traction exerted on the tool will pull the clamp forwards in the direction of the loosening sleeve and could thus open the clamp and release the tool even if the traction is lower than the standard limit of 22 N. In order to prevent any such inadvertent opening, the assembly formed by the clamp and the control pusher is advantageously provided with a snap fit holding device, arranged to offer a predetermined initial resistance to a movement forwards of the assembly from the working position. This device comprises resilient hooking means which abut on the hollow shaft and which can be made in different ways, by initially offering resistance to any movement of the clamp and the pusher which substantially exceeds the limit of 22 N. It is also this resistance that the operator has to overcome initially when he presses the button for opening the clamp to remove the tool. However, as soon as the snap fit has occurred, and the clamp has started to move forwards, the resistance offered by the button arises only from the axial component of the forces exerted by the loosening ring on the clamp and can thus be less than the initial force. In other words, after the snap fit, the operator exerts a reduced force on the button, which improves the comfort of use of the hand held piece.

BRIEF DESCRIPTION OF THE DRAWINGS

Other features and advantages of the present invention will appear from the following description, which shows a preferred embodiment and different variants by way of non-limiting example with reference to the annexed drawings, in which:

FIG. 5 is an axial cross-section of a part of the clamp of FIG. 2, FIG. 6 is a perspective view of a back guide bush visible in FIG. 1, FIG. 7 is a similar view to FIG. 3 and shows a variant of the loosening sleeve.

DETAILED DESCRIPTION OF VARIOUS EMBODIMENTS

Figure 1:
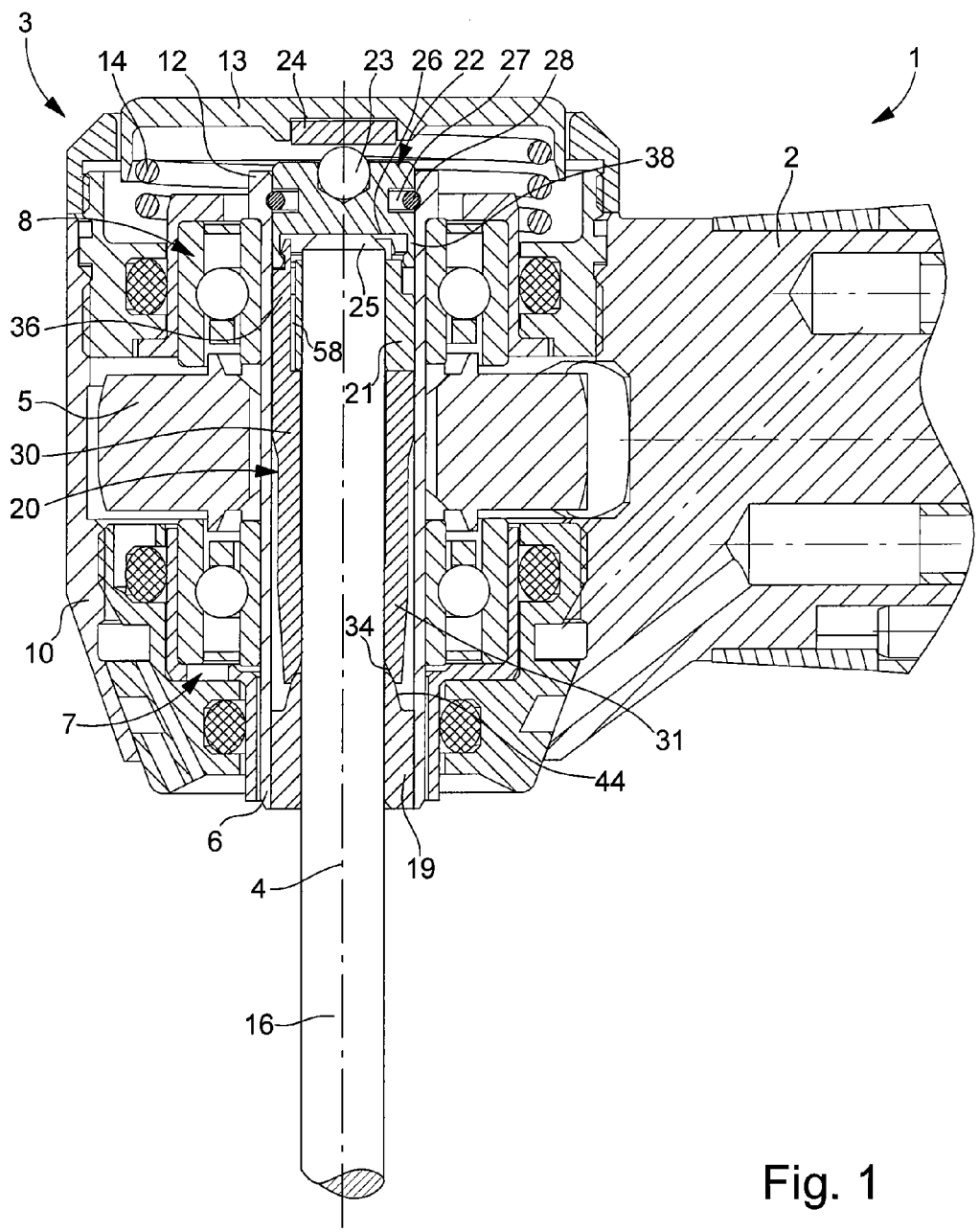
FIG. 1 is a schematic axial cross-section of the head of a hand held dental piece with a turbine according to a first embodiment of the invention.

The hand held piece 1 partially shown in FIG. 1 is of the air turbine type, comprising a handle 2 and a head 3 whose axis 4 is approximately perpendicular to the handle. The rotor 5 of the turbine is secured to a hollow shaft 6 carried by two bearings 7 and 8 in body 10 of head 3, to rotate about axis 4. Shaft 6 has the shape of a tube with a thicker back end 12, for abutting axially against back bearing 8. As usual, the head of the hand held piece is closed at the back, i.e. at the top in the position shown in FIG. 1, by a mobile cover thrust backwards to a stop by a return spring 14 and forming a manual control button 13. In order to hold the cylindrical shank 16 of a dental hold in a removable manner, in a position centred on axis 4, shaft 6 contains, from front to back, a loosening sleeve 19, a resilient clamp 20, a back guide bush 21 and a pusher 22. The latter carries on its back face a ball 23 against which a hard plate 24 of button 13 can abut when the button is pressed. Elements 19, 20 and 21 have a central bore which receives the tool shank 16, whereas the back end 25 of the shank abuts against a transverse wall 26 of pusher 22. An annular groove 27 is arranged in the periphery of pusher 22 for housing a wire spring 28 which is compressed radially by shaft 6 and is secured by snap fitting into a small inner groove of the shaft, thereby forming a snap fit holding device which maintains pusher 22 axially in the normal position.

Figure 2:
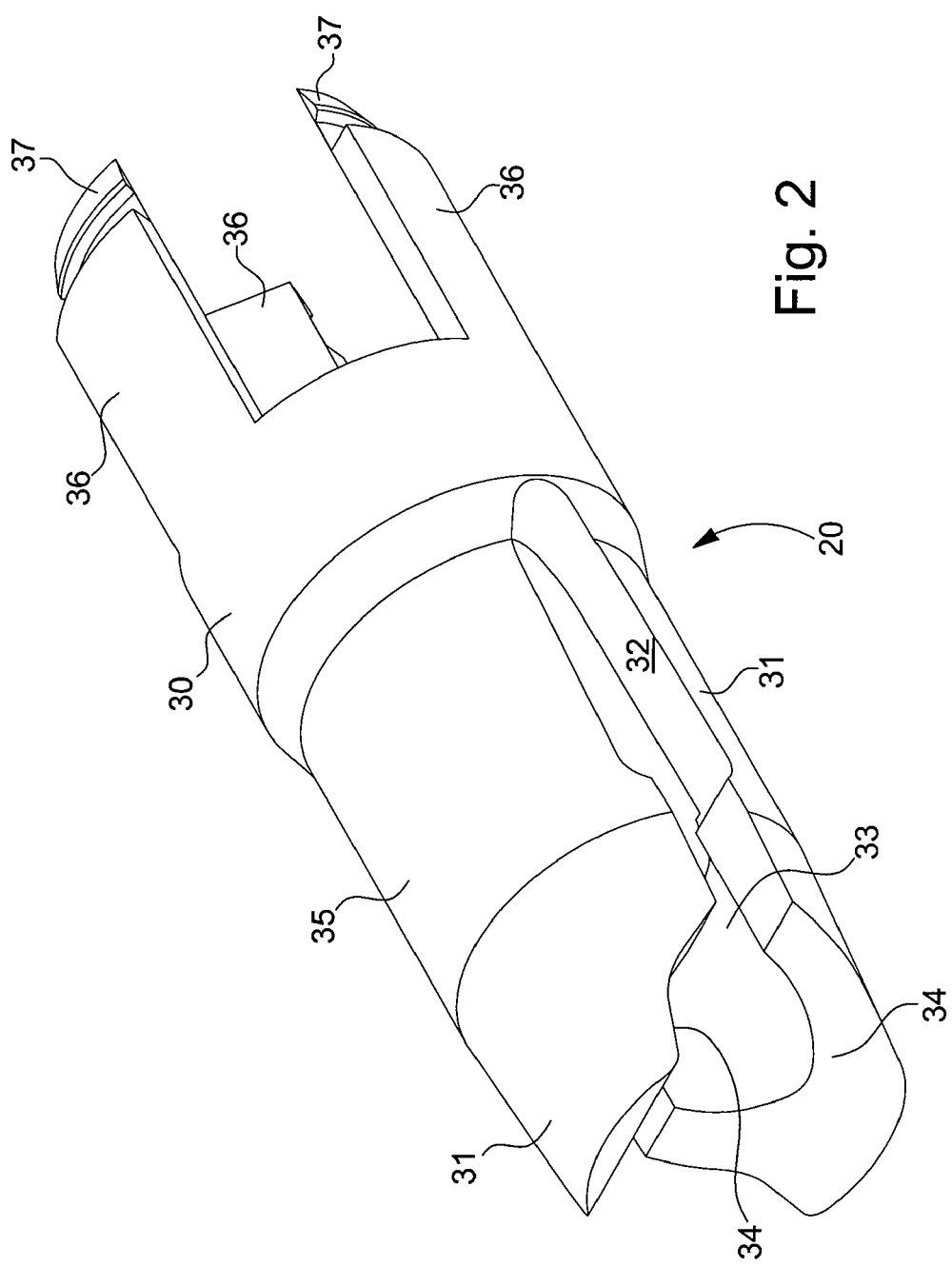
FIG. 2 is a perspective view of the clamp visible in FIG. 1.

Clamp 20 is a single piece construction, shown in FIG. 2, comprising an annular part 30 whose external cylindrical surface is fitted so as to slide in hollow shaft 6. Resilient jaws 31, which are two in number here, extend from the annular part, separated by longitudinal slots 32. In the front part of each jaw 31 there is an inner surface of substantially cylindrical shape, forming a gripping member 33 for gripping tool shank 16. In front of gripping member 33, the inner face of the jaw is tapered to form an oblique surface 34, inclined longitudinally and used for moving the jaws apart. The back part 35 of each jaw is thinned to make it flexible when a radial component force is exerted on oblique surface 34.

At rest, the diameter of the space comprised between gripping members 33 of the jaws is smaller than the standard diameter of shank 16 of the tools used, such that the jaws grip the shank resiliently when it is placed between them. The jaws are sized such that the gripping force and resulting friction are sufficient to offer resistance to any pull force that is higher than the standard limit.

The back of clamp 20 includes longitudinal arms 36 that are flexible radially, three in number here, which extend from annular part 30 and whose free end 37 has a hooking profile on the outer face. The function of these arms 36 is to hook clamp 20 to pusher 22. For this purpose, as can be seen in FIG. 1, the latter includes an annular edge 38 which extends in front of transverse wall 26 and has, inside, a complementary hooking profile to that of the clamp arms. Further, edge 38 abuts axially against arms 36 so as to be able to push the clamp forwards. The two hooking profiles and the flexibility of arms 36 are combined to ensure the required longitudinal holding of the clamp in any conditions in which the hand held piece is used, but to also allow separation by means of a greater force for the purpose of disassembly. End 37 of each arm 36 comprises a chamfer allowing the two parts to be reassembled by snap fitting together owing to the flexibility of arms 36.

Figure 3:
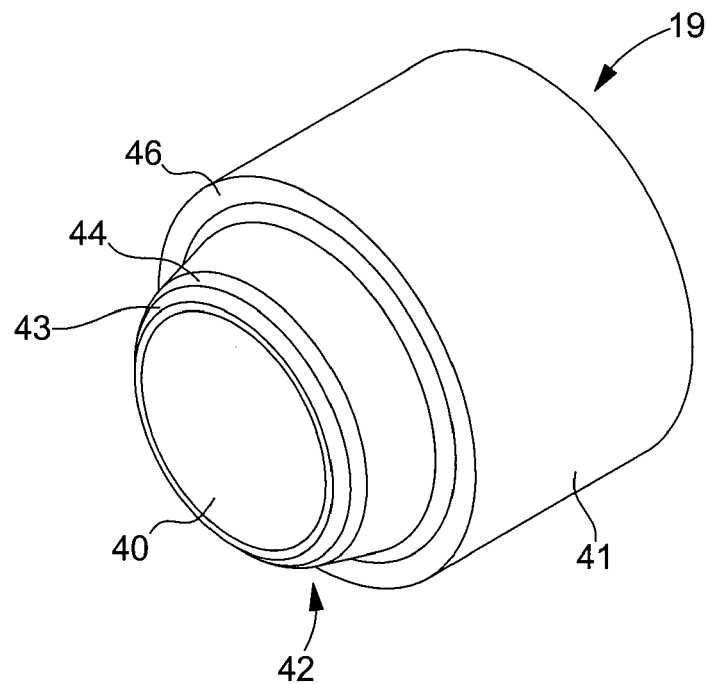
FIG. 3 is a perspective view of the loosening sleeve visible in FIG. 1.
Figure 4:
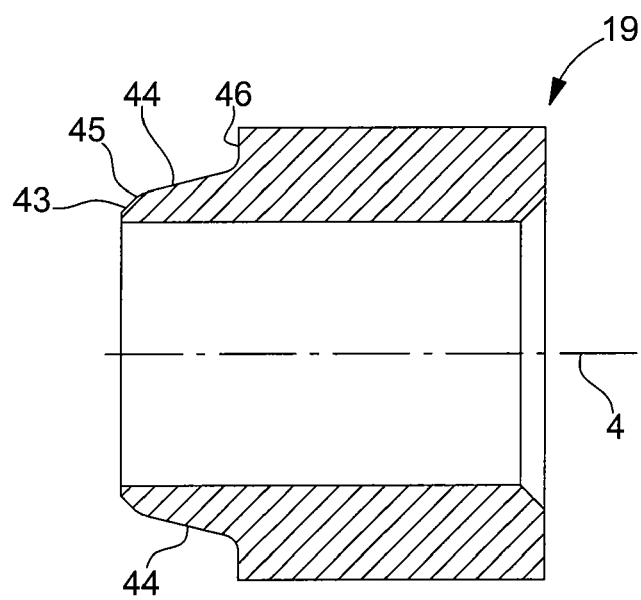
FIG. 4 is an axial cross-section of the sleeve of FIG. 3.

An embodiment of the loosening sleeve 19 is shown in detail in FIGS. 3 and 4. Its inner bore 40 is calibrated to receive the tool shank 16, such that sleeve 19 forms a front guide bush. Its outer surface 41 is cylindrical and is fitted with no play in hollow shaft 6, to which sleeve 19 is preferably welded. At the front, sleeve 19 includes an external cone 42 comprising two parts whose conicity angles are different, forming a first oblique surface 43 whose conicity angle in relation to axis 4 is greater than that of the second oblique surface 44. Surfaces 43 and 44 are connected by a rounded surface 45. Behind surface 44 there is a transverse surface 46. Surfaces 43 to 46 of the sleeve cooperate with the end of each jaw of clamp 20.

FIG. 5 is an enlarged cross-section of the free ends of jaws 31 of clamp 20 shown in FIGS. 1 and 2. On the inner face of the jaw, the surface of gripping member 33 is preceded by oblique surface 34 which is substantially plane in this example, but could also have a conical configuration in other embodiments. At the front, surface 34 is connected to a frontal surface 52 of the jaw by a rounded surface 51. Surfaces 34 and 51 of the jaw abut against the oblique surface 44 of loosening sleeve 19 to move the clamp jaws 31 apart. Frontal surface 52 can abut against the transverse surface 46 of sleeve 19 to stop the travel of the clamp in the open position.

FIG. 6 shows the shape of back guide bush 21, comprising a cylindrical bore 54 into which the tool shank 16 is guided with precision. Bush 21 has a peripheral surface 55 of cylindrical shape which fits into hollow shaft 6, to which it is fixed for example by welding. Between this surface and the back end 56 of bush 21 there is a section 57 of smaller diameter, leaving space for edge 38 of pusher 22. The cylindrical surface 55 is interrupted by three longitudinal grooves forming channels 58 into which the resilient arms 36 of the clamp pass with some radial play, as can be seen in FIG. 1, so that they can bend inwards to snap fit onto pusher 22. The clamp is secured to shaft 6 in rotation by its arms 36 snap fitted into channels 38.

During manufacture of the hand held piece, the presence of two fixed guide bushes 19 (i.e. the loosening sleeve) and 21 fixed in hollow shaft 6 advantageously allows the external surfaces of shaft 6 to be ground, by placing the shaft with hits two guide bushes on a reference shank occupying the place of tool shank 16. This enables the journals of bearings 7 and 8 to be ground on the shaft in order to ensure perfect concentricity with the bores of the two guide bushes.

The arrangement that has just been described works in the following way. In the working position that is shown in FIG.

1, clamp 20 does not abut on loosening sleeve 19. Instead of being welded to the shaft, the sleeve could be mounted so as to be adjustable longitudinally in order to adjust a space between the sleeve and the clamp. The dental tool shank 16 is guided laterally by the two bushes 19 and 21, abuts axially against pusher 22 at the back and remains held by the gripping members of clamp 20 against a pull force not exceeding the standard limit. This force is transmitted by arms 36 of the clamp to pusher 22, then by spring 28 to shaft 6 and to bearings 7 and 8. Ball 23 does not touch control button 13, such that shaft 6 driven by turbine 5 can rotate at high speed with no friction.

When the dentist wishes to change tools, he presses button 13 with his finger against the force of spring 14, which pushes pusher 22 and clamp 20 forwards. The snap fit of spring 28 in shaft 6 then offers an a resistant axial force greater than 22 N, for example 25 N or more, until the dentist overcomes the force and thus moves the clamp forwards, so that the ends of jaws 31 slide over oblique surfaces 44 of loosening sleeve 19 and are moved apart, which releases the tool. The inclination of oblique surfaces 34 and 44 of the clamp and the sleeve can be chosen such that the axial pressure that the dentist has to exert at that moment is relatively small, for reasons of comfort of use. The dentist therefore has only to exert a relatively large force at the start of the operation, to produce the initial snap fit.

Since clamp 20 is thus held open, the dentist can insert the shank 16 of a new tool, which will abut against pusher 22 and push it and the clamp upwards until spring 28 again snap fits in the groove of shaft 6 to hold the clamp in the working position.

FIG. 7 shows a variant of the loosening sleeve 19 illustrated by FIGS. 3 and 4. The oblique conical surfaces 43 and 44 are replaced here by opposite pairs of oblique plane surfaces 63 and 64, with a rounded cylindrical surface 65 between them. This arrangement works in the same way as the preceding example, but offers a wider linear contact between the jaws of the clamp and the loosening sleeve.

Figure 8:
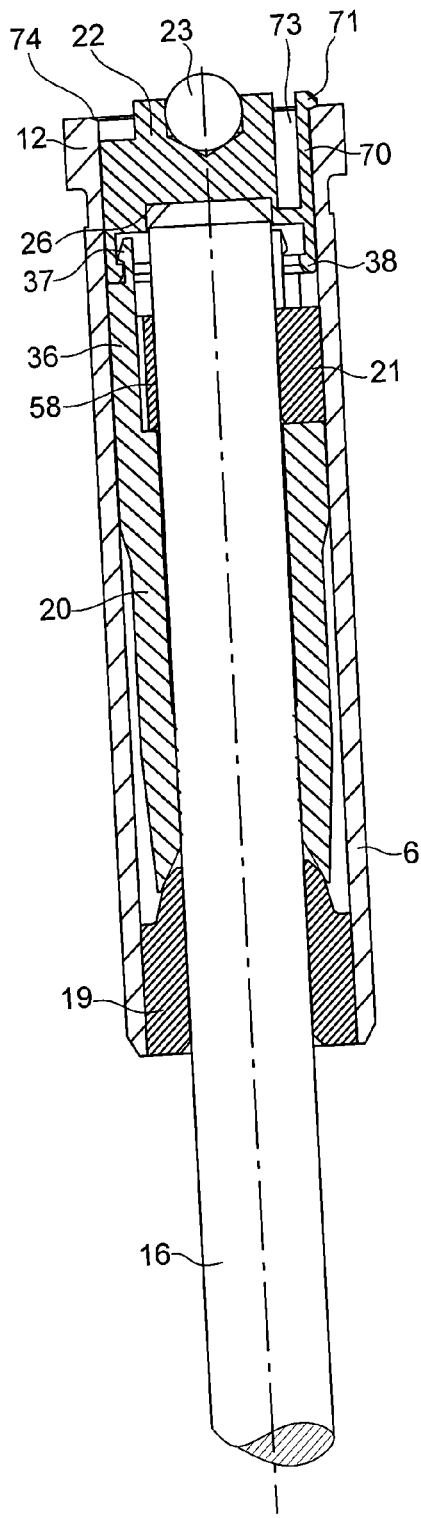
FIG. 8 is a schematic axial cross-section showing another embodiment of the invention.
Figure 9:
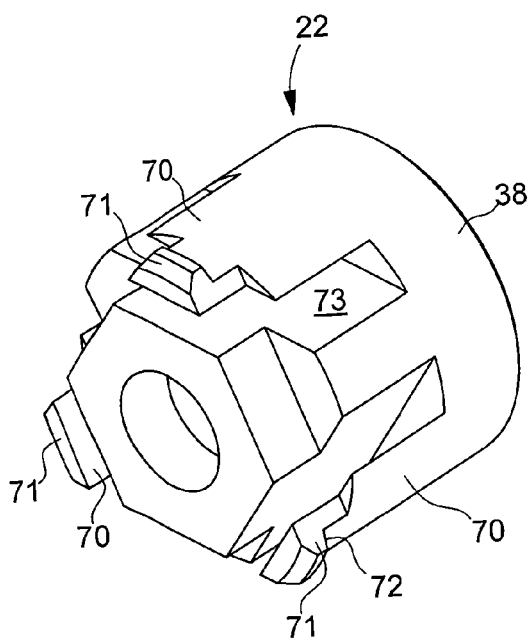
FIG. 9 is a perspective view of a pusher visible in FIG. 8.

FIGS. 8 and 9 show another embodiment of pusher 22 and its snap fit holding device on shaft 6. In order to replace the resilient hooking of pusher 22 by the snap fit of spring 28 shown in FIG. 1, the pusher is provided with flexible longitudinal arms 70, three in number here, each ending in a hook 71 capable of catching on the edge 74 of the back end 12 of shaft 6, owing to an oblique surface 72 of the hook. Each arm 70 is formed by making a notch 73 separating it from the central body of the pusher. The angle of inclination of oblique surface 72 and the resilient features of arm 70 determine a limit pull force, which must be greater than the minimum pull force of the tool as explained previously. As soon as the operator overcomes this force by pressing button 13 to open the clamp, a snap fit occurs via the decrease in resistant axial force and the operator then need only overcome the force exerted on clamp 20 by loosening sleeve 19. As in the preceding example, the flexible arms 36 of clamp 20 pass through the channels 58 of the back guide bush 21, driving the clamp in rotation, and catching on edge 38 of pusher 22 via their profiled end 37.

Other snap fit hold means can be provided instead of those shown in the drawings. For example, clamp 20 could have only two resilient arms at the back like arms 36, for catching on pusher 22, and to other resilient arms catching on another edge of back guide bush 21 or on the edges of orifices of shaft 6 to ensure longitudinal holding with a snap fit.

Among other possible variants, it will also be mentioned that the back guide bush 21 could be omitted in some cases, its function being taken over by annular part 30 of the clamp or by pusher 22, with a key connection to shaft 6 for ensuring driving in rotation. Moreover, the pusher could be welded to the clamp in any case where the assembly of these elements does not need to be capable of disassembly.

What is claimed is:

1. A hand held piece for dental or surgical use, comprising: a hollow shaft associated with means for driving in rotation, and in the hollow shaft are mounted a clamp for gripping a shank of a removable tool, a loosening sleeve and a sliding pusher placed in a rear end of the hollow shaft and controlled by a manual button for moving the clamp and the loosening sleeve towards each other, wherein the clamp includes an annular part and jaws arranged for gripping the shank of the removable tool via resilience in a working position, the jaws extending longitudinally from the annular part towards the loosening sleeve, wherein the loosening sleeve includes external oblique surfaces capable of abutting against free ends of the jaws to move the jaws apart, wherein the loosening sleeve is mounted in a front end of the hollow shaft, and wherein the clamp is slideably mounted in the shaft, and the jaws thereof are directed forwards, and the clamp is longitudinally connected to the pusher to enable an operator to move the clamp forwards to abut against the loosening sleeve.

2. The hand held piece according to claim 1, wherein the loosening sleeve is fixed in the hollow shaft and forms a front guide bush to the tool shank.

3. The hand held piece according to claim 1, wherein the pusher includes a transverse wall forming an axial stop member for the tool shank.

4. The hand held piece according to claim 1, wherein a back guide bush, provided with a cylindrical bore for receiving the tool shank, is fixedly mounted in the hollow shaft between the annular part of the clamp and the transverse wall of the control pusher and includes channels for longitudinal arms connecting the pusher to the clamp.

5. The hand held piece according to claim 4, wherein at least one of said longitudinal arms is resilient radially and provides a snap fit connection between the clamp and the pusher.

6. The hand held piece according to claim 1, wherein the assembly formed by the clamp and the pusher is provided with a snap fit hold device, arranged for offering a predetermined initial resistance to a movement of said assembly forwards from the working position.

7. The hand held piece according to claim 6, wherein the snap fit holding device includes resilient hooking means carried on the hollow shaft.

8. The hand held piece according to claim 7, wherein said resilient hooking means are formed by a spring arranged on the periphery of the pusher and cooperating with an inner groove of the hollow shaft.

9. The hand held piece according to claim 7, wherein said resilient hooking means are arranged on resilient longitudinal arms of the clamp or the control pusher and hook onto at least one edge of the hollow shaft.

10. The hand held piece according to claim 1, wherein the loosening sleeve is mounted on the tool side in a front end of the hollow shaft.

* * * * *